(12) United States Patent
Whitehurst

(10) Patent No.: US 6,626,932 B2
(45) Date of Patent: Sep. 30, 2003

(54) THERAPEUTIC LIGHT SOURCE AND METHOD

(75) Inventor: Colin Whitehurst, Cheshire (GB)

(73) Assignee: Photo Therapeutics LTD, Altrincham (GB)

(*) Notice: Subject to any disclaimer, the term of this patent is extended or adjusted under 35 U.S.C. 154(b) by 0 days.

(21) Appl. No.: 09/835,823

(22) Filed: Apr. 17, 2001

(65) Prior Publication Data

US 2002/0035386 A1 Mar. 21, 2002

(30) Foreign Application Priority Data

Apr. 17, 2000 (GB) .............................................. 0009489

(51) Int. Cl.$^7$ ................................................ A61N 5/06
(52) U.S. Cl. .......................................... 607/88; 607/80
(58) Field of Search .............................. 607/80, 88, 70, 607/92, 93

(56) References Cited

U.S. PATENT DOCUMENTS

| | | | | |
|---|---|---|---|---|
| 3,854,156 A | * | 12/1974 | Williams | 126/204 |
| 4,298,005 A | * | 11/1981 | Mutzhas | 250/503.1 |
| 4,444,189 A | | 4/1984 | Seiverd | |
| 4,444,190 A | | 4/1984 | Mutzhas | |
| 4,660,561 A | * | 4/1987 | Nielsen | 248/325 |
| 4,866,284 A | | 9/1989 | Frankena et al. | |
| 5,344,433 A | * | 9/1994 | Talmore | 607/88 |
| 5,441,531 A | * | 8/1995 | Zarate et al. | 604/21 |
| 5,503,637 A | * | 4/1996 | Kyricos et al. | 600/27 |
| 5,601,619 A | * | 2/1997 | Drechsler | 607/88 |
| 5,824,024 A | * | 10/1998 | Dial | 600/27 |
| 6,045,575 A | * | 4/2000 | Rosen et al. | 2/905 |
| 6,152,951 A | * | 11/2000 | Hashimoto et al. | 606/15 |
| 6,264,652 B1 | * | 7/2001 | Eggers et al. | 604/114 |
| 6,402,774 B1 | * | 6/2002 | Caldironi | 128/898 |

FOREIGN PATENT DOCUMENTS

| | | |
|---|---|---|
| DE | 76 12 890 | 12/1976 |
| DE | 28 04 228 A1 | 8/1979 |
| DE | 40 26 327 A1 | 2/1992 |
| DE | 196 47 676 A1 | 5/1998 |
| EP | 0 884 066 A2 | 12/1998 |
| GB | 2144996 A | 3/1985 |
| GB | 2 272 278 | 5/1994 |
| WO | WO 99/56827 A2 | 11/1991 |
| WO | WO 96/14899 | 5/1996 |
| WO | WO 97/40888 | 11/1997 |
| WO | 00/02491 | 1/2000 |

OTHER PUBLICATIONS

Copy of search report from European Patent Appl. No. 0130412.9–2305, 6 pages, dated Sep. 2, 2002.
Partial European Search Report for EP 01 30 3412, mailed Mar. 10, 2003 (4 pages).

* cited by examiner

*Primary Examiner*—Derek Boles
(74) *Attorney, Agent, or Firm*—Sterne, Kessler, Goldstein & Fox P.L.L.C.

(57) ABSTRACT

A light source for therapy, such as photodynamic therapy, comprises one or more low pressure or medium/high pressure discharge tubes. In one aspect, the light source comprises a non-planar array of substantially straight tubes. In another aspect, the light source comprises one or more such tubes mounted in a housing having an aperture allowing part of the patient to be located within the housing.

62 Claims, 7 Drawing Sheets

FIG. 9A
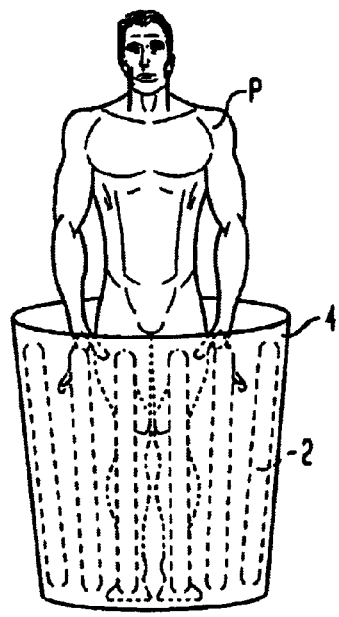
FIG. 9B
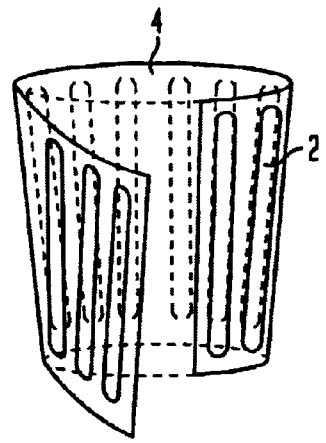
FIG. 10A  FIG. 10B
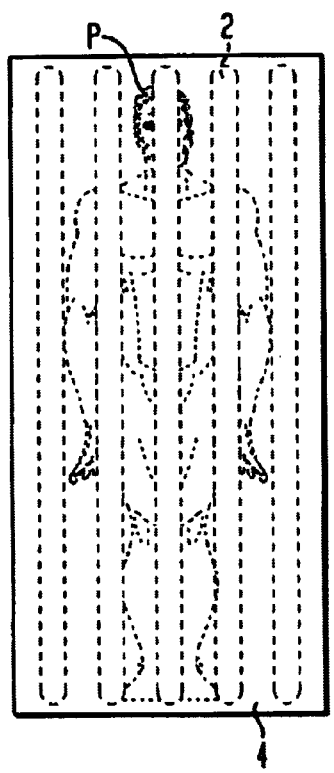
FIG. 11A  FIG. 11B
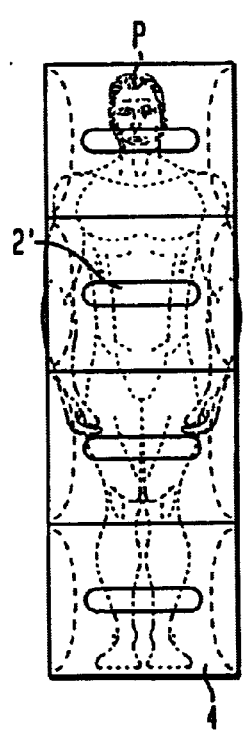
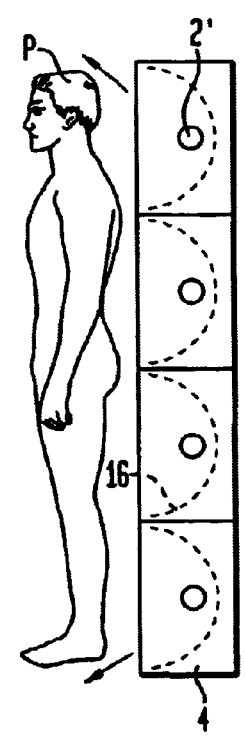

THERAPEUTIC LIGHT SOURCE AND METHOD

BACKGROUND OF THE INVENTION

The present invention relates to a non-coherent light source for use in therapy such as photodynamic therapy (PDT), particularly but not exclusively for treating large external surfaces of a patient, and/or a method of use thereof.

Photodynamic therapy involves the administration of a photosensitising drug to an affected area, and its subsequent irradiation with light—see for example 'The Physics of Photodynamic Therapy' by B C Wilson and M S Patterson, Physics in Medicine & Biology 31 (1986) April No. 4, London GB.

The document WO 97/40888 proposes the use of one or more fluorescent tubes to emit yellow, orange and/or red wavelengths in a lamp for PDT. However, the coefficient of absorption of many PDT drugs for PDT, and of human tissue, is relatively low in these wavelengths, so that the light will have a high penetration depth and is unsuitable for treating superficial conditions. Moreover, the activation efficiency of most PDT drugs is low at these wavelengths and the light intensity available from fluorescent tubes is also comparatively low, which will lead to long treatment times.

The document WO 99/56827 discloses a light source for PDT treatment or diagnosis of the scalp or face, comprising U-shaped fluorescent tubes which emit preferably blue light. This light source would be expensive to manufacture as the U-shaped tubes would have to be manufactured specifically for this application.

STATEMENT OF INVENTION

According to one aspect of the present invention, there is provided a therapeutic light source comprising a non-planar array of substantially straight fluorescent tubes arranged to emit light substantially within the visible spectrum.

In one embodiment, the array may be mounted on a surface curved perpendicular to the length of the tubes.

In another embodiment, the array may be mounted on at least two planar surfaces set at an angle to one another.

According to another aspect of the present invention, there is provided a therapeutic light source comprising one or more fluorescent grid lamps each comprising a tube having a plurality of folds in the same plane.

According to another aspect of the present invention, there is provided a therapeutic light source comprising a discharge tube and a concave reflector arranged to concentrate light on an area to be treated. In one embodiment, the light source is mounted in a housing having an aperture allowing part of the patient to be located within the housing.

According to another aspect of the present invention, there is provided a light source for PDT including one or more medium/high pressure discharge lamps arranged to emit narrow bandwidth light directly, such that it impinges on a patient with an intensity of at least 3 mW/cm$^2$, preferably between 10 and 100 mW/cm$^2$, and no greater than approximately 200 mW/cm$^2$. Such medium/high pressure discharge lamps can produce a greater intensity than low-pressure fluorescent lamps, while still providing the advantage of narrow bandwidth light over a large area without the need for intervening optics.

Preferably, the bandwidth of the medium/high pressure discharge lamp(s) is 160 nm or less.

Preferably, the arc length of the medium/high pressure discharge lamp(s) is at least 15 mm.

The or each medium/high pressure discharge lamp may be straight or have a folded or serpentine shape.

In either aspect, preferably the one or more lamps are arranged in a housing having a window or aperture through which light impinges on the patient, and preferably a reflector arranged to reflect light specularly or diffusely from the lamps through the window or aperture. The reflector is preferably arranged to provide a uniform output.

The present invention includes a method of use of the light source for PDT, in which a topical photosensitizer such as 5-aminolaevulinic acid (5-ALA) is applied to the affected area of the patient and light from the light source is subsequently applied. Preferably, the method is used to treat superficial oncological or non-oncological conditions. Preferably, the method is used to treat one or more of actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, warts (recalcitrant, verruca vulgaris or verruca plantaris), alopecia areata or hirsutism. Preferably, the total treatment time is no greater than one hour per session.

The present invention further includes a method of cosmetic or partially cosmetic treatment with a photosensitizing drug for portwine stain removal and hair restoration/removal, and without a photosensitizing drug for skin rejuvenation, wrinkle removal or biostimulation (including wound healing).

BRIEF DESCRIPTION OF THE DRAWINGS

Specific embodiments of the present invention will now be described with reference to the accompanying drawings, in which:

FIGS. 9a and 9b are schematic diagrams of a lamp, respectively in use and with a door open for access, using fluorescent tubes for treatment of the lower half of a patient's body;

FIGS. 10a and 10b are respectively frontal and side schematic views of a lamp using fluorescent tubes arranged on the reflective inner surface of a walk-in booth;

FIGS. 11a and 11b are respectively frontal and side schematic views of a lamp using medium/high pressure discharge tubes, for treatment of one side of the patient in a standing position;

MODES FOR CARRYING OUT THE INVENTION

Figure 1:
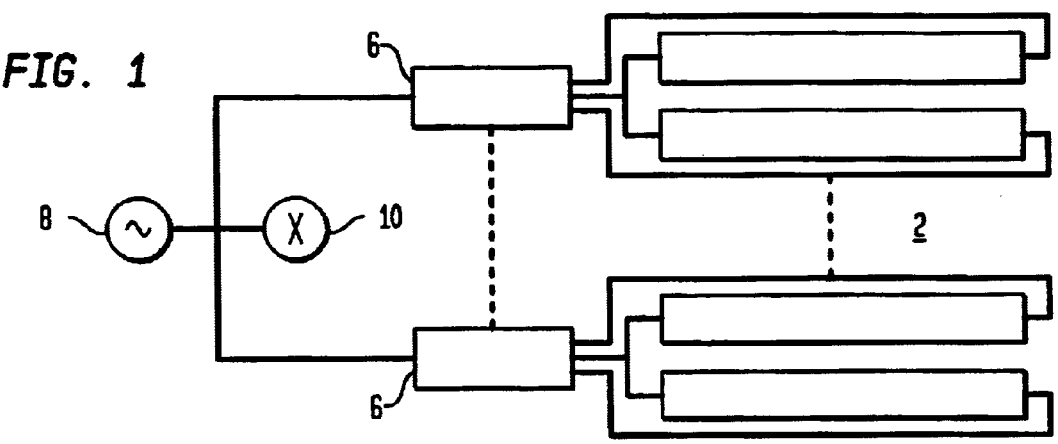
FIG. 1 is a schematic circuit diagram of a fluorescent tube array in an embodiment of the present invention.
Figure 2:
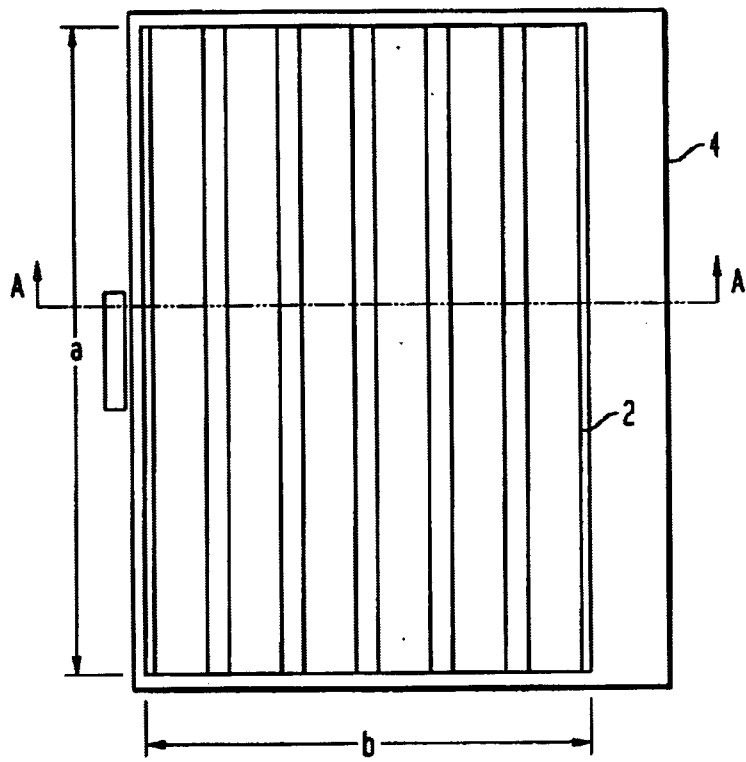
FIG. 2 is a front view of the tube array in a housing.
Figure 3:
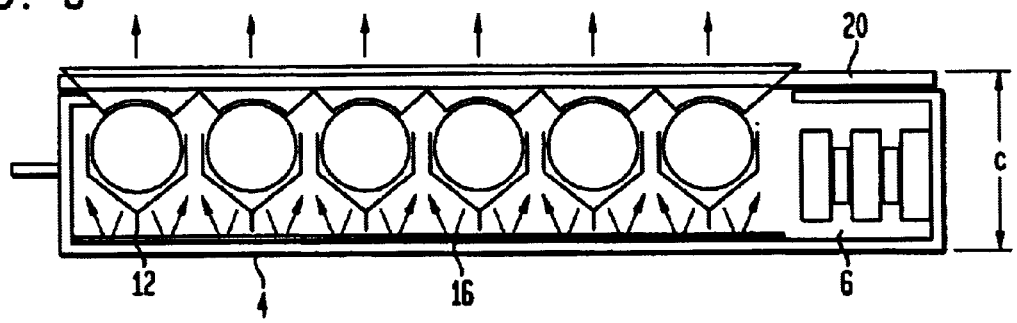
FIG. 3 is a cross-section along the plane A—A perpendicular to FIG. 2.

In an embodiment shown in FIGS. 1 to 3, six similar fluorescent tubes 2 are mounted parallel in an array in a generally cuboid hollow housing 4 made of polished stainless steel. The tubes 2 are electrically connected to electronic ballasts 6 for initiating and maintaining current flow through the tubes 2. The ballasts 6 are powered by an a.c. mains power supply 8. A fan 10, also driven by the mains power supply 8, is arranged to draw air through vents (not shown) in the housing 4 so as to cool the tubes 2.

Each of the tubes is securely engaged in a resilient mounting bracket 12 at each end attached to a back wall 14 of the housing 4. On the internal surface of the back wall 14 is a white diffuse reflector 16 arranged to reflect diffusely towards the front of the light emitted by the tubes 2. The diffuse reflector 16 may be made of a white self-adhesive plastic sheet (e.g. Fablon™) or a removable sheet of paper or other material which can easily be replaced if it becomes dirty. Instead of a diffuse reflector, a non-planar specular reflector may be used to provide a uniform beam, such as a dimpled metal reflector as is often used in high power security lamps.

The housing 4 has an aperture 18 in its front surface substantially conforming in size and shape to the extent of the light-emitting portions of the array of tubes 2. The aperture 18 is covered by a transparent or translucent lid 20, for example of plastic such as clear polycarbonate, e.g. Makrolon™. The lid 20 is removable to allow access to and replacement of the tubes 2. The lid 20, when in place, serves to protect the internal components and the patient from each other. Preferably, the housing 4 is placed horizontally with the aperture 18 facing upwards and the patient lies on or rests the affected area on the lid 20, which is strong enough to support the patient or affected area.

The lid 20 may filter the light emitted by the tubes 2 before it impinges on the patient. For example, the lid 20 may comprise or include a layer of material which filters out part of the emission spectrum of the tubes 2. The material may filter out UV radiation and/or parts of the visible spectrum which do not excite the relevant photosensitising drug. The layer of material may be removably attached to a support forming part of the lid 20, such as guide rails, to allow the filtering layer to be exchanged for another filtering layer, or removed completely.

In one example, the length a of the housing 4 is 600 mm, the width b is 300 mm, and the depth c is 70 mm.

Figure 4:
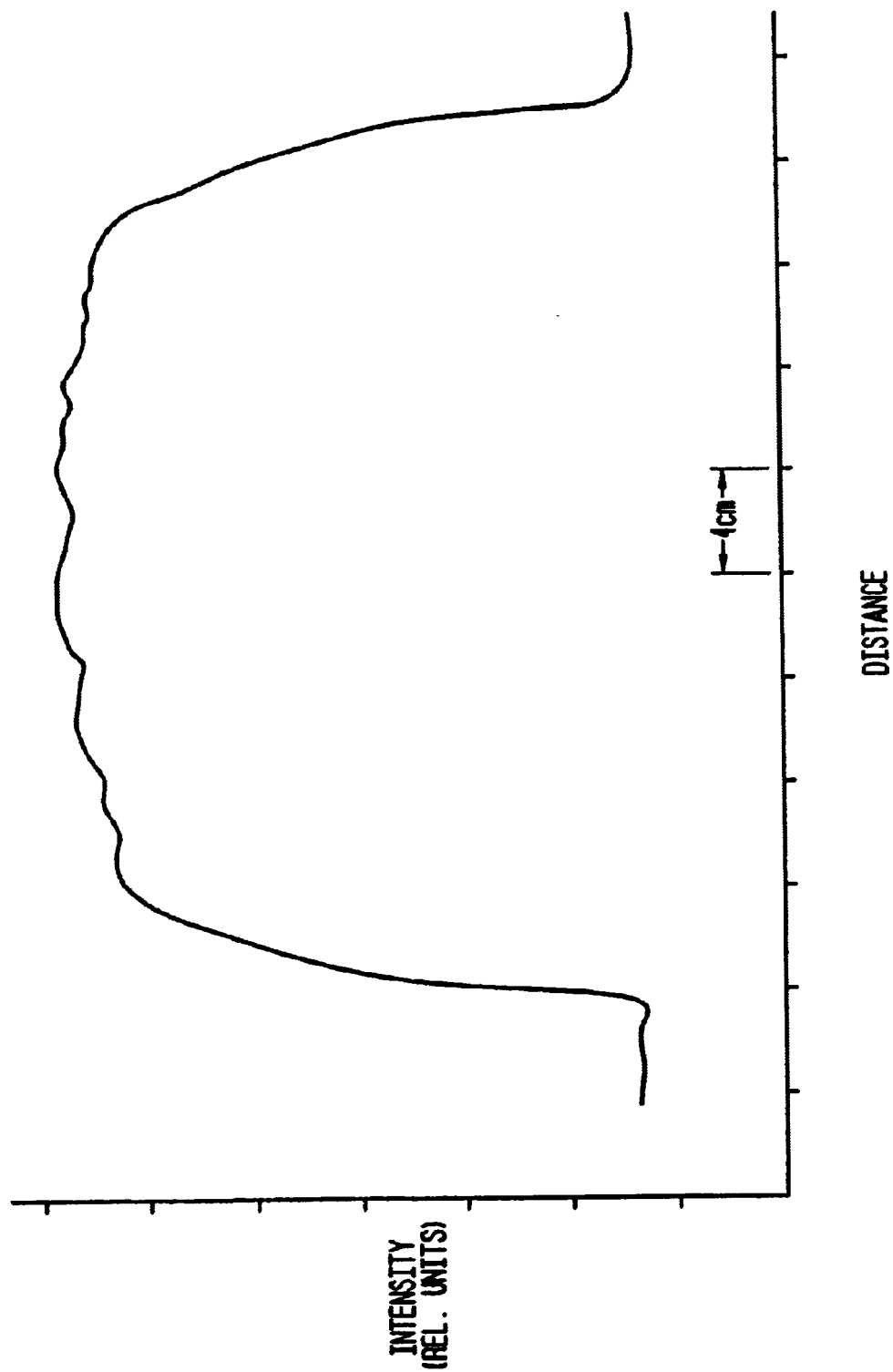
FIG. 4 is a profile of the beam intensity of the tube array across the treatment field.

The diffuse reflector 16 and the spacing of the tubes 2 gives a beam profile as shown in FIG. 4. In this example, the tubes are 38 mm in diameter and there is a 15 mm gap between adjacent tubes. Across the width (in the direction of the width b of the housing 4) of the treatment field, which extends over about 30 cm, the beam intensity varies by no more than approximately 6%. This degree of uniformity minimises the risk of some areas of the patient's skin receiving less than the threshold light dose, which is important to prevent recurrence of the disease being treated.

Figure 5:
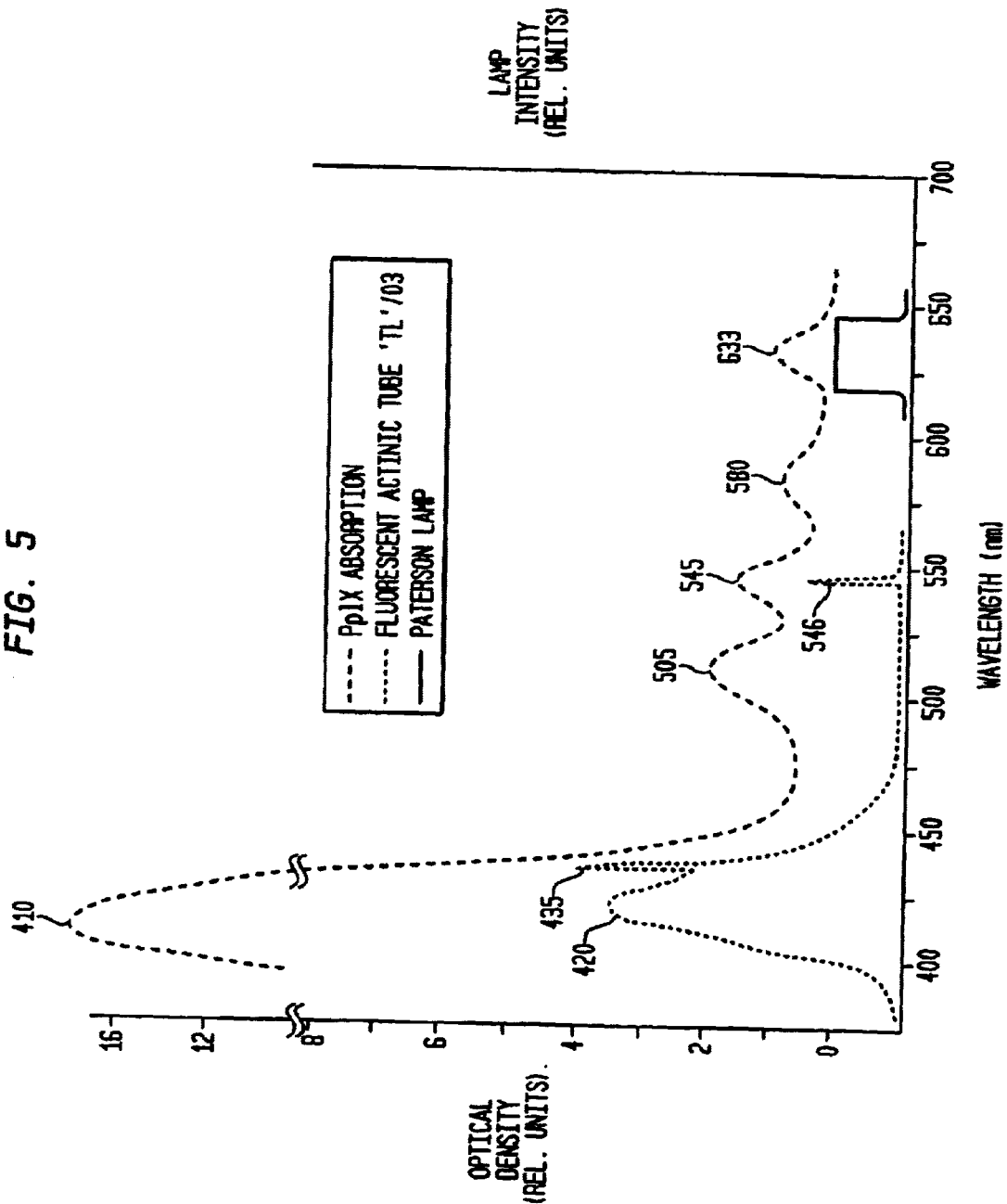
FIG. 5 shows the absorption spectrum of PpIX, the emission spectrum of a prior art lamp and the emission spectrum of the fluorescent tubes of the tube array.

The tubes 2 have a fluorescent coating selected so as to emit light with a narrow spectrum coincident with an absorption peak of a photosensitive drug, and substantially confined within a range of 350 to 500 nm, most preferably 400 to 450 nm. FIG. 5 shows the output spectrum of a suitable fluorescent tube, reference TL/03, such as part no. TLK 40/03 available from Philips, which is commercially available and used in diazo printing. The spectrum shows the main peak at 420 nm with additional very narrow, low energy peaks at 435 nm and 546 nm.

Superimposed on the graph, but in relative units of optical density shown on the left hand side of the graph, is the absorption spectrum of PpIX. It can readily be seen that the absorption peak at 410 nm is much greater and broader than the absorption peak at 633 nm, or the other absorption peaks at 545 nm and 580 nm with which the output of the lamp described in WO97/40888 may coincide. Hence, for the same area of skin to which 5-ALA, a precursor of PpIX, is topically applied, the light from the lamp of the embodiment will have a substantially shorter penetration depth, and an activation efficiency approximately 20 times greater. In the treatment of superficial diseases of the skin by PDT, this will result in substantially no damage to underlying layers of skin and substantially shorter treatment times as a result of more efficient absorption by the affected tissue.

A method of treatment for superficial cases of actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism will now be described. A cream or solution containing a photosensitising drug such as 5-ALA is applied topically under medical supervision to the affected area of the skin of the patient, or administered intravenously or orally. For large areas, the patient may be immersed in a bath of solution. The affected area may then be covered for a period of 3 to 6 hours, or up to 24 hours if the treatment is to be continued the next day, to prevent removal of the drug and carrier, or activation by sunlight. The area is then uncovered and exposed to light from the lamp as described in any of the embodiments for a period of 15 to 30 minutes. The treatment may then be repeated as necessary, for a total of 1 to 3 treatments or more, depending on the severity and type of the condition. This method is particularly suitable for the treatment of patients with very large lesions or multiple lesions extending over a large area.

The lamp may also be used for fluorescence detection (photodiagnosis).

The lamp may also be used for cosmetic or partially cosmetic treatment with a photosensitizing drug for portwine stain removal and hair restoration/removal, and without a photosensitizing drug for skin rejuvenation, wrinkle removal or biostimulation (including wound healing).

The lamp may be scaled up or down in size so that the effective treatment area (as defined for example as the extent of substantially uniform illumination as shown in FIG. 4) extends over the whole body of a patient or just the area to be treated. The whole-body size is particularly suitable for the treatment of psoriasis, mycosis fungoides and pre-malignant skin diseases.

The lamp may include an electro-optical detector arranged to monitor the light dose delivered and to switch off the light emission when a target dose is reached. Alternatively, or additionally, the detector is arranged to monitor the instantaneous light intensity and to vary the electrical power supplied to the tubes so as to maintain the intensity within predetermined limits, and/or to switch off the light emission if a maximum limit is exceeded.

In an alternative embodiment, TL/52 fluorescent tubes, having a peak emission at approximately 450 nm, are used in place of the TL/03 tubes. However, the TL/52 tubes are less desirable because of the lower absorption of PpIX around this wavelength.

In an alternative embodiment, low pressure 'grid lamps' comprising low pressure mercury or xenon arc lamps may be used. These 'grid lamps' are formed of narrow bore silica or glass tubes, with an outside diameter of less than approximately 13 mm and preferably approximately 9 mm, folded in a serpentine shape to give an overall arc length of between a few centimeters and 10 meters. Preferably, the tube is made from quartz, which transmits UV light. A phosphor is therefore coated onto the outside of the tube, or onto the bore of a second, outer concentric tube.

In any of the embodiments which use fluorescent tubes, the full circumference of each tube, or at least 70% thereof, is coated with phosphor. Where only part of the circumference is coated with phosphor, the remaining part may be coated with reflective material to reflect the discharge radiation onto the phosphor-coated part of the tube. Such tubes are arranged to concentrate light towards the patient.

The phosphor gives an emission wavelength substantially coincident with photosensitiser absorption spectra, as shown in Table 1 below.

TABLE 1

Photosensitiser Absorption Spectra

| Photosensitiser | Red absorption band | Red peak | Blue/green peak |
|---|---|---|---|
| Naphthalocyanines | 780–810 | | |
| Chalcogenopyrilium dyes | 780–820 | | |
| Phthalocyanines (e.g. ZnII Pc) | 670–720 | 690 | |
| Tin ethyl etiopurpurin (SnET$_2$) | 660–710 | 660–665 | 447 |
| Chlorins (e.g. N-Aspartyl chiorin e6 or NPe6) | 660–700 | 664 | |
| Benzoporphyrin derivative (BPD) | | 685/690 | 456 |

TABLE 1-continued

Photosensitiser Absorption Spectra

| Photosensitiser | Red absorption band | Red peak | Blue/green peak |
|---|---|---|---|
| Lutetium texaphrin (Lu-Tex) | | 735 | |
| Al(S$_1$/S$_2$/S$_3$/S$_4$)Pc | 660–710 | 670/685 | 410,480 |
| Photofrin | | 625/630 | 405 |
| Protoporphyrin IX (PpIX) (from 5/δAminolaevulinic Acid (5 ALA)) | | 635 | 410,505,540, 580 |
| Tetra m-hydroxyphenyl Chlorin (mTHPC) | | 650 | 440, 525 |

Two or more phosphors may be mixed together in the coating to give the required emission spectra. Different phosphor coatings available from BHK, Inc. Claremont USA have the following properties shown below in Table 2:

TABLE 2

BHK Phosphor Peak Emissions and Bandwidths

| Peak Emission Wavelength (nm) | Bandwidth (nm) |
|---|---|
| 406 | 41 |
| 418 | 29 |
| 430 | 114 |
| 460 | 105 |
| 494 | 170 |

Alternative phosphor coatings available from Jelight Company, Inc., Irvine, Calif., USA have the properties shown below in Table 3:

TABLE 3

Jelight Phosphor Peak Emissions and Bandwidths

| Peak Emission Wavelength (nm) | Bandwidth (nm) |
|---|---|
| 400 | 37 |
| 413 | 34 |
| 420 | 34 |
| 446 | 112 |
| 446, 525, 580 | discrete peaks |
| 447 | 32 |
| 450 | 49 |
| 455 | 62 |
| 460 | 105 |
| 473 | 136 |
| 479 | 75 |
| 482 | 138 |
| 495 | 223 |

In yet another alternative embodiment, medium/high pressure discharge tubes are used in place of the low pressure fluorescent tubes 2, with the driving circuitry replaced accordingly. As medium/high pressure discharge tubes generally give a much higher intensity output than fluorescent tubes, the former are more widely spaced apart and have individual reflectors arranged to provide a uniform illumination. The medium/high pressure tubes have a gas fill selected to activate the photosensitiser in use, examples of which are shown above in Table 1. Sample gas and vapour fills are shown below in Table 4:

TABLE 4

Gas/Vapour Fills

| Type | Fill | Emission Wavelengths* (nm) |
|---|---|---|
| Medium Pressure mercury plus additive: | gallium | 400–430 |
| | thallium | 530–550 |
| | cadmium | 440, 550, 580 |
| | gallium + thallium | 400–420, 440, 450, 540 |
| | indium | 450–460 |
| | gallium + lead | 400–430 |
| High Pressure | sodium vapour | 560–640 |
| | sodium vapour, plus xenon or mercury | 600–760 |
| Medium Pressure Rare Gas | neon | 585–670 |
| | argon | 416–488, 697 |
| | krypton | 427–587 |
| Medium Pressure Vapour | cadmium | 480, 508 |
| | mercury | 405, 436, 546, 577 |
| | caesium | 455, 852 |
| | zinc | 636 |
| | thallium | 535 |
| | potassium | 766 |

*Discrete peaks shown as single peak wavelengths, emission bands shown as ranges.

Another possible fill is mercury-argon or mercury-xenon at medium or high pressure, which gives superposition of the two emission spectra together with a pressure-broadened continuum across the visible spectrum.

In an alternative embodiment, an array of high-pressure metal halide lamps may be used where the arc burns in a dense vapour of mercury and rare earth halides, giving a peak emission in the range 400 to 650 nm.

Possible alternative arrangements of the tubes in the above embodiments will now be described. In each of these arrangements, straight tubes or grid lamp tubes are used, as such shapes are commercially available at low cost. Where fluorescent tubes, grid lamp tubes or medium/high pressure discharge tubes are described, these may be any of the tubes of such type described above. In these arrangements, fluorescent tubes may be replaced by medium/high pressure discharge tubes by increasing the spacing between tubes and providing an individually shaped reflector for each tube, except where providing such an individual reflector is impractical due to shape and size constraints. Likewise, medium/high pressure discharge tubes may be replaced by fluorescent tubes, except where this would lead to an intensity too low for practical photoherapeutic or diagnostic applications.

Figure 6A:
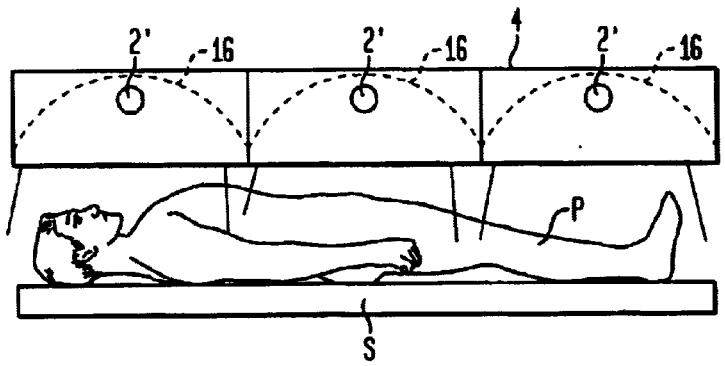
FIGS. 6a and 6b are respectively longitudinal and transverse schematic diagrams of a lamp using medium/high pressure discharge tubes for full-length treatment of one side of a patient.
Figure 6B:
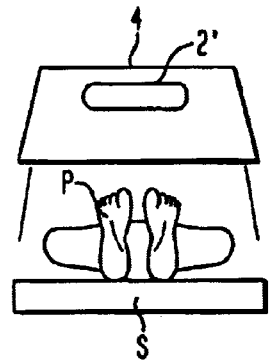

FIGS. 6a and 6b show a lamp using medium/high pressure discharge tubes 2', for full-length treatment of one side of a patient P. The lamp comprises three such tubes arranged parallel to each other and perpendicular to the length of the patient in a housing 4. Each tube has a curved reflector 16 arranged behind it so as to generate an approximately uniform illumination of the patient P lying on a surface S.

Figure 7A:
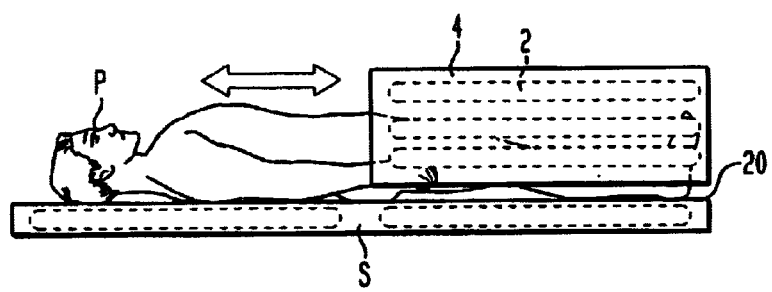
FIGS. 7a and 7b are respectively longitudinal and transverse schematic diagrams of a lamp using straight fluorescent discharge tubes for treatment of a section of a patient.
Figure 7B:
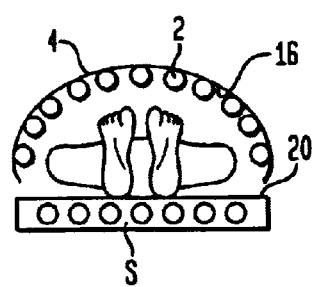
Figure 8A:
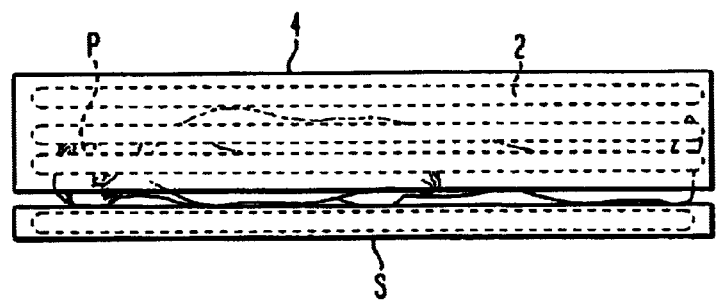
FIGS. 8a and 8b show a variant of the arrangement of FIGS. 7a and 7b, for full-length treatment of a patient.
Figure 8B:
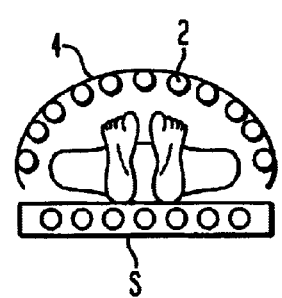

FIGS. 7a and 7b show a lamp using straight fluorescent discharge tubes 2, for treatment of a section of the patient P. The tubes are arranged parallel to each other and to the length of the patient P, on the inner reflective surface 16 of a curved housing 4 which can be slid relative to the patient P along the length of the patient so as to illuminate the desired section of the patient P. The surface S on which the patient rests may be the lid(s) 20 of flat lamp(s) using fluorescent tubes 2 as described above. FIGS. 8a and 8b show a variant in which the tubes 2 and the housing 4 extend substantially over the whole length of the patient P for full-length treatment; in this case, the housing 4 does not need to be slidable.

FIGS. 9a and 9b show a lamp using fluorescent tubes 2, for treatment of the lower half of a patient's body. The tubes are arranged on the inner reflective surface of an housing 4 within which the patient P stands. The housing 4 is a slightly tapered cylinder with a diameter which increases with height so as to keep the distance between the patient's skin and the tubes 2' approximately constant. The housing 4 may have a door for access, as shown in FIG. 9b in an open position.

FIGS. 10a and 10b show a lamp using fluorescent tubes 2, arranged on the reflective inner surface of a housing 4 in the form of a walk-in booth, which may be oval, circular, rectangular, hexagonal, or other polygonal in cross-section, of constant diameter with height. The booth includes a door, the inner surface of which carries some of the tubes. The tubes extend approximately vertically.

FIGS. 11a and 11b show a lamp using medium/high pressure discharge tubes 2' for treatment of one side of the patient P. This arrangement is similar to that shown in FIGS. 6a and 6b except that four parallel tubes are used and the lamp stands upright to illuminate one side of a standing patient P.

Figure 12A:
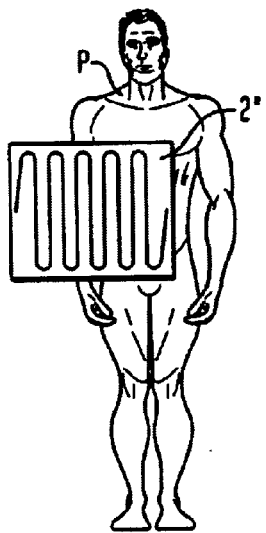
FIGS. 12a and 12b are respectively frontal and side schematic views of a grid lamp positioned to illuminate part of the patient to be treated.
Figure 12B:
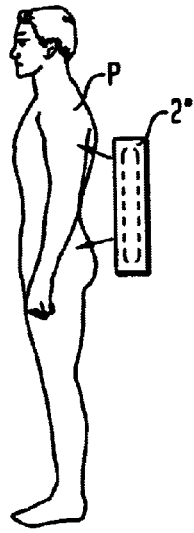
Figure 13A:
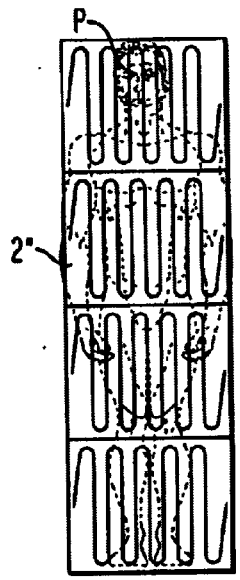
FIGS. 13a and 13b are respectively frontal and side schematic views of a lamp comprising four substantially coplanar grid lamps arranged in a row, to illuminate the whole length of a patient.
Figure 13B:
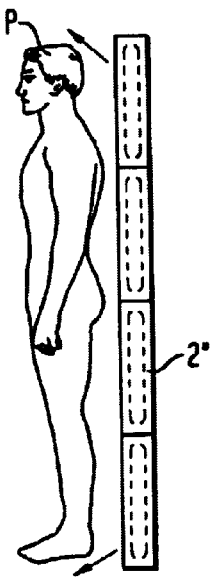

FIGS. 12a and 12b show a grid lamp 2" in an embodiment of the invention, positioned to illuminate part of the patient to be treated. FIGS. 13a and 13b show an alternative lamp comprising four such substantially coplanar grid lamps 2" arranged in a row, to illuminate the whole length of a patient.

Figure 14:
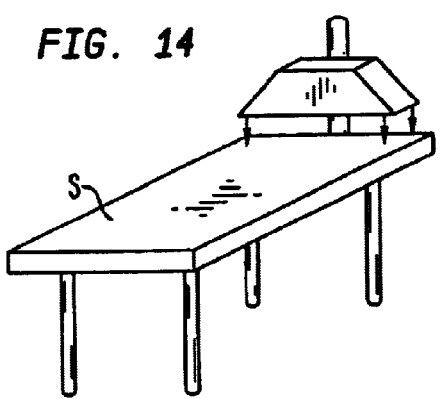
FIG. 14 is a perspective view of a lamp using medium/high pressure discharge tubes for facial treatment, mounted on a bed.
Figure 15:
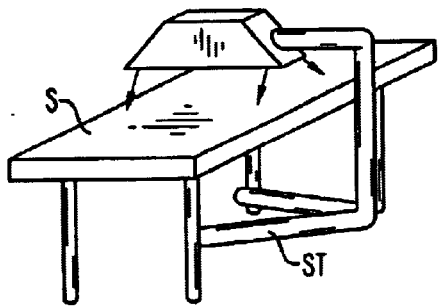
FIG. 15 is a perspective view of a free-standing version of the arrangement of FIG. 14.

FIGS. 14 and 15 show a lamp using medium/high pressure discharge tubes 2' according to any of the above embodiments. In FIG. 14, the lamp is mounted at one end of a bed S so that its height above the bed S is adjustable, for facial treatment of a patient lying on the bed. In FIG. 15, the lamp is mounted on a stand ST and is adjustable in height, for treatment of a selected part of a patient P lying on the bed S.

Figure 16:
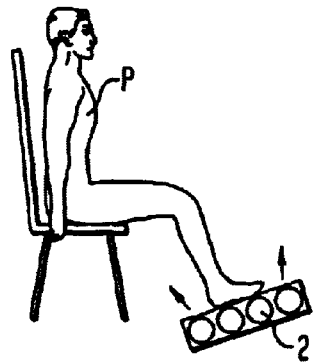
FIGS. 16 to 18 are side views, partially in cross-section, of lamps comprising an array of parallel fluorescent discharge tubes, for treatment of the foot, lower leg and full leg respectively.
Figure 17:
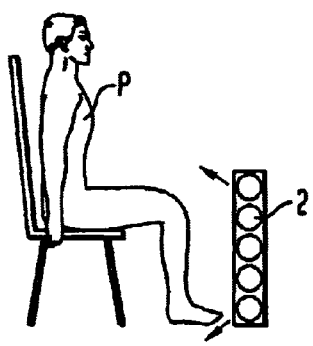
Figure 18:
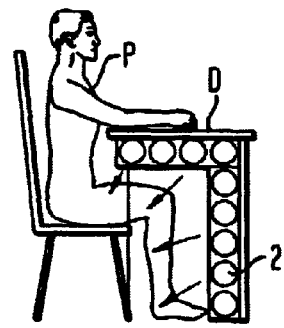

FIGS. 16 to 18 show a lamp comprising an array of parallel fluorescent tubes 2 for treatment of a sitting patient P. The arrangement of FIG. 16 is used for treatment of the sole of the patient's foot or feet. The arrangement of FIG. 17 is used for treatment of the patient's lower leg(s). The arrangement of FIG. 18 comprises two flat arrays of such tubes, arranged on the underside and inner back surface of a desk-like structure D, for full-leg treatment of the patient. The desk-like structure D is advantageous for long treatments as it allows the patient to rest comfortably and read, eat or perform other activities on the desk top.

Figure 19A:
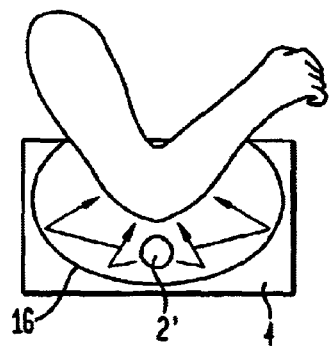
FIGS. 19a to 19c are respectively a cross-section in the plane of an arm, a top view and a vertical cross-section perpendicular to the plane of the arm of a patient, of a lamp using a medium/high pressure tube for treatment of the elbows of a patient.
Figure 19B:
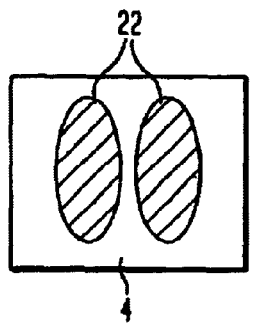
Figure 19C:
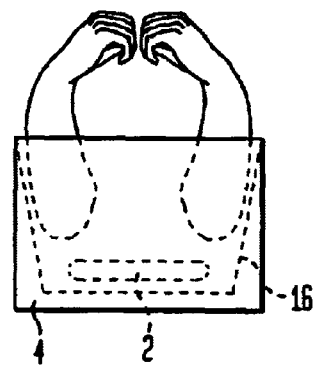

FIGS. 19a to 19c show a lamp comprising a medium/high pressure discharge tube 2', for treatment of one or both elbows. The lamp comprises a cuboid housing 4 having two similar apertures 22 on one face, to allow the elbows to be inserted into the housing 4. A medium/high pressure discharge tube 2' is positioned with the reflector, towards the bottom of the housing. Light from the tube 2' is concentrated onto the elbows of the patient P by the reflector 16.

Figure 20A:
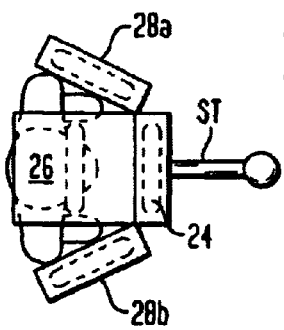
FIGS. 20a and 20b are top and side views, respectively, of a lamp comprising medium/high pressure discharge tubes, for treatment of the face and/or scalp of a patient in a sitting position.
Figure 20B:
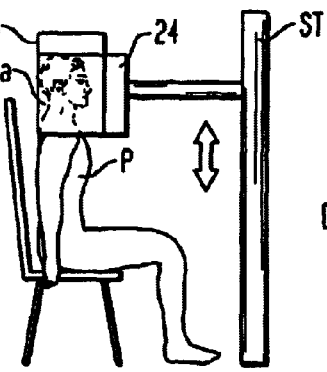

FIGS. 20a and 20b show a lamp comprising medium/high pressure discharge tubes 2' for treatment of the face and/or scalp. The lamp has a front-facial portion 24, comprising a medium/high pressure discharge tube 2' and a reflector 16, for directing light onto the face of the patient P from the front. A scalp portion 26 and left and right side-facial portions 28a, 28b are attached by hinges to the front-facial portion 24, each portion comprising a medium/high pressure discharge tube 2' and reflector 16 for directing light onto the scalp, left side of the face and right side of the face respectively. The front-facial portion 24 is slideably attached to a stand ST for vertical adjustment to the head height of the patient P, preferably when sitting.

Figure 21:
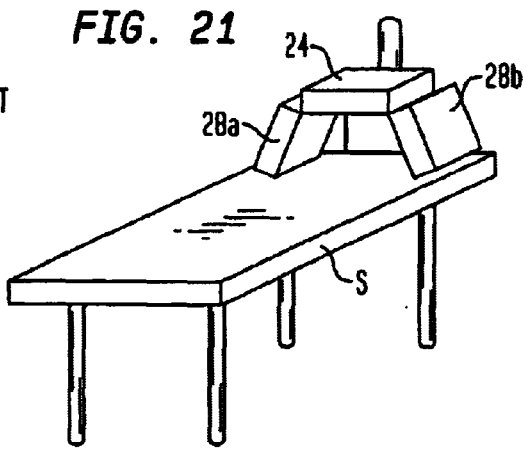
FIG. 21 is a perspective view of a lamp similar to that of FIGS. 20a and 20b, but mounted on a bed for treatment of a patient lying down.

FIG. 21 shows a lamp similar to that of FIGS. 20a and 20b, except that it is arranged for facial and/or scalp treatment of a patient P when lying down. The vertical support is mounted on a bed S, instead of being free-standing, and the lamp is rotated by 90° so as to correspond to the position of the patient's head when lying down.

The above embodiments are described purely by way of example and variants thereof may fall with the spirit and scope of the present invention as defined by the following claims.

What is claimed is:

1. A light source for therapy or diagnosis of a patient, comprising a non-planar array of substantially straight discharge tubes arranged to emit light substantially in the visible spectrum at an intensity of at least 3 mW/cm² on the patient.

2. A light source as claimed in claim 1, wherein the tubes are fluorescent tubes.

3. A light source as claimed in claim 1, wherein the tubes are arranged to emit light of wavelengths substantially confined within the range 350 to 500nm.

4. A light source as claimed in claim 3, wherein the tubes are arranged to emit light of wavelengths substantially confined within the range 400 to 450 nm.

5. A light source as claimed in claim 1, wherein the tubes are arranged along a surface curved perpendicular to the length of the tubes.

6. A light source as claimed in claim 5, wherein the tubes are mounted on the curved inner surface of a housing arranged to cover at least part of the length of a patient.

7. A light source as claimed in claim 6, wherein the housing is moveable along the length of the patient so as to irradiate a selected part of the length of the patient.

8. A light source as claimed in claim 5, wherein the tubes are mounted on the curved inner cylindrical surface of a housing dimensioned so as to irradiate only the lower half of a standing patient.

9. A light source as claimed in claim 5, wherein the tubes are mounted on the curved inner surface of a housing dimensioned so as to allow a patient to stand within the housing such that substantially the whole length of the patient's body is irradiated.

10. A light source as claimed in claim 1, wherein the tubes are arranged on at least two planar surfaces set an angle to one another.

11. A light source as claimed in claim 10, wherein the tubes are mounted on the underside of a substantially horizontal surface under which the patient's legs rest when the patient is in a sitting position, and on a substantially vertical surface facing the patient's lower legs when the patient is in a sitting position.

12. A light source as claimed in claim 10, wherein the tubes are mounted on a first substantially planar member and on a second substantially planar member attached by a moveable joint to the first member.

13. A light source as claimed in claim 12, wherein the first planar member is arranged to irradiate the face of a patient from the front.

14. A light source as claimed in claim 12, wherein the second planar member is arranged to irradiate the scalp of a patient.

15. A light source as claimed in claim 12, wherein the second planar member is arranged to irradiate the face of a patient from the side.

16. A light source for therapy or diagnosis of a patient, comprising one or more discharge lamps arranged within a housing, an aperture allowing a part of the patient's body to be inserted into the housing, and a concave reflector mounted within a housing and arranged to concentrate light from the one or more lamps onto the part of the patient's body when inserted into the housing.

17. A light source for therapy or diagnosis of a patient, comprising one or more fluorescent grid lamps each comprising a tube having a plurality of folds in the same plane.

18. A light source for therapy of a patient, comprising at least one medium/high pressure discharge lamp and a housing arranged to allow a part of the patient to be brought into close proximity to the at least one medium/high pressure discharge lamp such that light therefrom impinges on said part of the patient with an intensity of at least 3 mW/cm², the light having a bandwidth of less than approximately 160 nm.

19. A light source according to claim 18, wherein the or each medium/high pressure discharge lamp has an arc length of at least 15 mm.

20. A light source according to claim 18, wherein the or each lamp is a medium pressure lamp.

21. A light source according to claim 20, wherein the lamp contains mercury vapour.

22. A light source according to claim 21, wherein the lamp further contains a vapour of one or more elements selected from a group comprising gallium, thallium, cadmium, indium and lead.

23. A light source according to claim 22, wherein the lamp contains a vapour of one or more elements selected from a group comprising cadmium, mercury, caesium, zinc, thallium and potassium.

24. A light source according to claim 23, wherein the lamp contains a rare gas.

25. A light source according to claim 24, wherein the rare gas consists of one or more of a group comprising neon, argon and krypton.

26. A light source according to claim 18, wherein the or each lamp is a high pressure lamp.

27. A light source according to claim 26, wherein the lamp contains sodium vapour.

28. A light source according to claim 27, wherein the lamp further contains xenon.

29. A light source according to claim 27, wherein the lamp further contains mercury.

30. A light source according to claim 1, wherein the intensity fluctuation across the treatable area of the patient is approximately 10% or less.

31. A light source according to claim 30, wherein the intensity fluctuation is approximately 6% or less.

32. A light source according to claim 18, including a substantially regular array of similar said lamps.

33. A light source according to claim 1, including a diffuse reflecting surface arranged to reflect light towards the patient.

34. A light source according to claim 18, including a housing containing said one or more lamps, and an aperture allowing light from the one or more lamps onto the patient.

35. A light source according to claim 34, wherein said aperture has a transparent or translucent cover.

36. A light source according to claim 35, wherein said cover is arranged to filter part of the output spectrum of the one or more lamps.

37. A light source according to claim 36, wherein the cover comprises or includes a detachable filter.

38. A light source for therapy or diagnosis of a patient, comprising a plurality of low pressure discharge lamps mounted within a housing allowing light from the lamps to impinge on the patient, and a transparent or translucent cover over the aperture, the cover comprising or including a detachable filter.

39. A light source according to claim 1, wherein said light source is used in the treatment of superficial skin conditions.

40. A light source according to claim 39, wherein the treatment is for cosmetic purposes.

41. A light source according to claim 1, wherein said light source is used in the treatment of one or more of: actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism.

42. A light source according to claim 41, wherein the condition is superficial.

43. A light source according to claim 39, wherein said light source is used in photodynamic therapy.

44. A light source according to claim 40, wherein said light source is used in photodynamic therapy.

45. A light source according to claim 41, wherein said light source is used in photodynamic therapy.

46. A light source according to claim 43, wherein the affected area of the patient is treated with PpIX.

47. A light source according to claim 44, wherein the affected area of the patient is treated with PpIX.

48. A light source according to claim 45, wherein the affected area of the patient is treated with PpIX.

49. A method of cosmetic treatment of one of a human and animal body, comprising the steps of:
applying a photosensitizer to an area to be treated; and
illuminating the area with light from a light source according to claim 1.

50. A method of medical treatment of one of a human and animal body, comprising the steps of:
applying a photosensitizer to the area to be treated; and
illuminating the area with light from a light source according to claim 1.

51. A light source according to claim 16, wherein said light source is used in the treatment of one or more of: actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism.

52. A light source according to claim 17, wherein said light source is used in the treatment of one or more of: actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism.

53. A light source according to claim 18, wherein said light source is used in the treatment of one or more of: actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism.

54. A light source according to claim 38, wherein said light source is used in the treatment of one or more of: actinic/solar keratoses, Bowen's disease, superficial basal cell carcinoma, squamous cell carcinoma, intraepithelial carcinoma, mycosis fungoides, T-cell lymphoma, acne and seborrhoea, psoriasis, eczema, nevus sebaceous, viral infections such as herpes simplex, molluscum contagiosum, and warts (recalcitrant, verruca vulgaris or verruca plantaris), alopecia areata or hirsutism.

55. A method of cosmetic treatment of one of a human and animal body, comprising the steps of:
applying a photosensitizer to an area to be treated; and
illuminating the area with light from a light source according to claim 16.

56. A method of cosmetic treatment of one of a human and animal body, comprising the steps of:
applying a photosensitizer to an area to be treated; and
illuminating the area with light from a light source according to claim 17.

57. A method of cosmetic treatment of one of a human and animal body, comprising the steps of:
applying a photosensitizer to an area to be treated; and
illuminating the area with light from a light source according to claim 18.

58. A method of cosmetic treatment of one of a human and animal body, comprising the steps of:
applying a photosensitizer to an area to be treated; and
illuminating the area with light from a light source according to claim 38.

59. A method of medical treatment of one of a human and animal body, comprising the steps of:
applying a photosensitizer to the area to be treated; and
illuminating the area with light from a light source according to claim 16.

60. A method of medical treatment of one of a human and animal body, comprising the steps of:
applying a photosensitizer to the area to be treated; and
illuminating the area with light from a light source according to claim 17.

61. A method of medical treatment of one of a human and animal body, comprising the steps of:
applying a photosensitizer to the area to be treated; and
illuminating the area with light from a light source according to claim 18.

62. A method of medical treatment of one of a human and animal body, comprising the steps of:
applying a photosensitizer to the area to be treated; and
illuminating the area with light from a light source according to claim 38.

* * * * *